US010643597B2

(12) United States Patent
Hupke et al.

(10) Patent No.: US 10,643,597 B2
(45) Date of Patent: May 5, 2020

(54) METHOD AND DEVICE FOR GENERATING AND PROVIDING AN AUDIO SIGNAL FOR ENHANCING A HEARING IMPRESSION AT LIVE EVENTS

(71) Applicant: Sennheiser electronic GmbH & Co. KG, Wedemark (DE)

(72) Inventors: Robert Hupke, Hannover (DE); Marcel Nophut, Hannover (DE); Jürgen Peissig, Hannover (DE)

(73) Assignee: Sennheiser electronic GmbH & Co. KG, Wedemark (DE)

( * ) Notice: Subject to any disclaimer, the term of this patent is extended or adjusted under 35 U.S.C. 154(b) by 0 days.

(21) Appl. No.: 16/361,395

(22) Filed: Mar. 22, 2019

(65) Prior Publication Data

US 2019/0295525 A1 Sep. 26, 2019

(30) Foreign Application Priority Data

Mar. 22, 2018 (DE) ........................ 10 2018 106 904

(51) Int. Cl.

| | |
|---|---|
| ***A61F 11/06*** | (2006.01) |
| ***G10K 11/16*** | (2006.01) |
| ***H03B 29/00*** | (2006.01) |
| ***G10K 11/178*** | (2006.01) |

(52) U.S. Cl.
CPC .................. *G10K 11/17854* (2018.01); *G10K 2210/1081* (2013.01)

(58) Field of Classification Search
CPC ................................................ G10K 11/17854
See application file for complete search history.

(56) References Cited

U.S. PATENT DOCUMENTS

2008/0201138 A1* 8/2008 Visser ................. G10L 21/0208 704/227
2014/0172421 A1* 6/2014 Liu ...................... H04R 1/1083 704/227
2015/0039303 A1* 2/2015 Lesso ...................... G10L 15/20 704/233
2017/0193976 A1* 7/2017 Mohammad ......... G10K 11/178
2018/0123813 A1* 5/2018 Milevski ................. H04S 7/303
2018/0132037 A1* 5/2018 McGibney ............... H04R 3/02

FOREIGN PATENT DOCUMENTS

EP 2 625 621 8/2016

* cited by examiner

*Primary Examiner* — Simon King
(74) *Attorney, Agent, or Firm* — Haug Partners LLP

(57) ABSTRACT

A method for generating and providing an audio signal, including receiving a first audio signal via an external microphone of a headphone or earphone, and receiving a second audio signal via a wireless interface. The first audio signal includes a portion reproduced via loudspeakers. The second audio signal corresponds to the portion reproduced via loudspeakers and is received before the corresponding portion of the first audio signal. A propagation time difference is determined between the first audio signal and the second audio signal. The second audio signal is modified by adaptive filtering and temporal shifting such that the propagation time difference between the first and second modified audio signal is substantially compensated. The adaptive filtering models an acoustic transmission of the first audio signal and a modified second audio signal is obtained. The modified second audio signal is inverted, then it is provided via the headphone or earphone.

25 Claims, 4 Drawing Sheets

METHOD AND DEVICE FOR GENERATING AND PROVIDING AN AUDIO SIGNAL FOR ENHANCING A HEARING IMPRESSION AT LIVE EVENTS

The present application claims priority from German Patent Application No. DE 10 2018 106 904.9 filed on Mar. 22, 2018, the disclosure of which is incorporated herein by reference in its entirety.

FIELD OF THE INVENTION

The invention relates to an improvement of a hearing impression of the audience at live events. For example, live events are concerts presented to audiences on open-air or indoor venues such as event halls or concert halls. Live events are characterized in particular by the fact that sound and sounds such as music or speech of one or more performers are provided to the audience in a substantially unchanged manner amplified by a speaker system.

In particular, the audience often wishes to better understand and/or hear individual instruments and/or voices of the performing persons in relation to other instruments or ambient sounds. However, such individual wishes usually cannot be considered.

Although a performance on a stage is usually recorded with multiple microphones, it is provided after mixing with a mixing console through loudspeakers to the entire audience. Thus, individual preferences of individual viewers cannot be addressed.

From EP2625621B1, a method and a device for enhancing sound are known, wherein a smartphone or similar computer is used. The microphone of the smartphone records an acoustic sound, which is emitted in response to a primary sound signal and transmitted through a space, and a wireless signal encoded with the primary sound signal is received by means of an antenna. Based on the recorded acoustic signal and the primary signal encoded in the wireless signal, an impulse response of the room is then estimated and a delay between the acoustic signal and the primary sound signal encoded in the wireless signal is calculated. The primary sound signal encoded in the wireless signal is then delayed according to the estimated delay, before it is output via headphones synchronously with the acoustic signal. Thus, it supplements the acoustic environmental signal that the listener hears despite the headphones. However, the listener has to make sure that the smartphone with the microphone is located in close proximity to the body, e.g. clipped to the listener's waist. Also, in following the teachings of EP2625621B1, it turns out that the known system may be improved.

SUMMARY OF THE INVENTION

The following invention relates to the demand of the audience for an improved individual hearing impression even at live events. This relates to sound of the respective live event, where the invention is based on the recognition of the fact that the exact position of the microphone may be of high importance, but also to a user's individual speech communication.

To this end, an audio mixer or mixing console receives an audio signal that may have two or more audio tracks, mixes and transmits this signal as a second audio signal via a wireless interface, in particular a WLAN interface or mobile network interface. The transmitted signal may have one, two or more audio tracks. Furthermore, this signal is provided to one or more loudspeakers, such as e.g. a public address system, which emits a corresponding sound signal. A data signal comprising information about the audio tracks of the second audio signal may also be transmitted via the wireless interface.

According to a method for generating and providing an audio signal, the second audio signal transmitted as a radio signal via the wireless interface is received first. Moreover, a first audio signal is received. The first audio signal is herein preferably a sound signal that is converted into an electrical audio signal by one or more audio sensors, in particular microphones. The first audio signal comprises a portion that is emitted from loudspeakers, such as e.g. hall or stage loudspeakers or the like. Therefore, this portion largely corresponds to the second audio signal. According to the invention, a propagation time difference between the first and the second audio signal is determined, and the second audio signal is adaptively filtered and delayed, based on the determined propagation time difference. This results in a modified second audio signal. The adaptive filtering herein models an acoustic transmission of the first audio signal. The second audio signal is preferably delayed such that the propagation time difference between the first and the modified second audio signal is substantially compensated, i.e. it is at or below a predefined threshold. This threshold is preferably 0 seconds, but may be slightly higher, e.g. up to 100 ms, because such a small difference is not yet perceived as disturbing.

In some embodiments, the delayed and modified second audio signal is inverted after that. The resulting signal may be replayed as a compensation signal via the headphone or earphone or it may be used for compensating ambient sound e.g. in a telephone conversation. The compensation signal compensates ambient sound, in particular also for higher frequencies than conventional active noise cancellation (ANC) could, because with the second audio signal transmitted via radio, an essential part of the ambient sound in the situation described is already known here in advance. This allows preparing the adaptive filter for frequencies of later received portions of the first audio signal, so that it may react quicker and thus generate counterphase waves also for shorter waves. Thus, this embodiment provides a kind of radio-assisted ANC. In an embodiment, in one operating mode the compensation signal may be output together with the second audio signal, so that the replayed signal is even better freed from ambient noise. In another operating mode, portions of the modified second audio signal may be modified and then output, like e.g. single audio tracks, in order to emphasize them more. As a result, an individual audio signal that does not affect other listeners in their individual listening wishes is available to a listener or viewer.

Thus, a first audio signal that corresponds to a certain proportion or even predominantly to the sound emitted via the loudspeaker is received, and a second audio signal is received from a mixing console or audio mixer as a radio signal via a wireless interface. The second audio signal is received earlier than the first audio signal, since a wireless interface allows faster transmission than sound propagation through the air. By compensating for the propagation time difference, two received audio signals are now available that offer the possibility of improving a hearing impression or individualizing it by means of adaptation. This may be done by adding or subtracting the two audio signals, as appropriate, so that they can be provided together to a listener.

Receiving the second audio signal via a wireless interface makes it possible to receive the second audio signal before the first airborne audio signal. In an embodiment, the wireless interface is a WLAN interface or a mobile network interface, in particular according to the 3G, 4G or 5G standard. As a result, the second audio signal can be received so early that an immediate processing of the second audio signal is made possible and the processed second audio signal can be merged with the first audio signal, which cannot be delayed.

According to an embodiment, the first audio signal is received via an audio sensor, in particular a microphone, which is in some embodiments an external microphone of a headphone that may be connected to a mobile telephone.

According to a further embodiment, the propagation time difference is determined by cross-correlation. The cross-correlation can be easily and quickly calculated and implemented on a device.

According to an embodiment, the modified second audio signal, or inverted modified second audio signal respectively, is output via a headphone, which may in particular be connected to a mobile telephone that performs the signal processing.

According to a further embodiment, the merged audio signal is output via a closed headphone. This has the advantage that a complete suppression of environmental noise is possible, so that only the merged audio signal is supplied to a listener but no other ambient noise bypassing the headphone. Alternatively, the headphone is an on-ear headphone or in-ear headphone, allowing the viewer to perceive certain instruments or voices stronger or weaker through the merging of the first and second audio signals, while still perceiving ambient sounds and directly entering sound waves from the stage speakers.

According to a further embodiment, the second audio signal comprises two or more audio tracks, wherein the modifying comprises attenuating, removing or partially removing at least one audio track of the second audio signal. By this it is possible for the user to select just one or more interesting audio tracks in order to particularly emphasize or attenuate in this manner e.g. certain instruments or a performer's voice in the merged audio signal.

According to a further embodiment, the first and/or second audio signal before adaptive filtering may be further modified. The further modifying comprises amplifying, adding, partially adding, attenuating, removing and/or partially removing of at least one adjustable frequency or at least one adjustable frequency range to the first and/or second audio signal. In this manner, e.g. bass or treble in the merged audio signal can be individually amplified or attenuated.

According to a further embodiment, the second audio signal is adapted during the modifying such that the portion that corresponds to an audio track of the second audio signal and/or at least an adjustable frequency and/or frequency range is removed or partially removed when merging the first and the modified second audio signal. Accordingly, a frequency range or audio track individually adjustable for a user is thus removed by the second audio signal according to the per se known method of active noise suppression. According to an embodiment, an operating mode is provided in which the entire second audio signal can be reduced in or removed from the merged audio signal. In this case, the entire sound signal coming from the stage is compensated, so that only other sound signals picked up by the microphone are contained in the merged signal. In this way, the user can hear his or her surroundings even at very loud performances, and e.g. have a conversation with another person nearby at a rock concert. In this embodiment, a microphone of the smartphone or an external microphone of a headphone or earphone may be used.

According to a further embodiment, an additional data signal comprising information about the audio tracks of the second audio signal is received via the wireless interface. The single audio tracks may be shown for the user e.g. on a mobile terminal that is preferably used for executing this method, so that the user can easily select audio tracks to be amplified, attenuated or completely suppressed.

Moreover, the invention relates to a software product for configuring a computer or a processor, e.g. an audio mixer, to execute the method for generating and providing an audio signal. In addition, the invention relates to a device, in particular a mobile device, that is adapted for executing the method for generating and providing an audio signal. The mobile device may be e.g. a mobile phone or a headphone. The device comprises a microphone for recording a first audio signal and a wireless interface module for receiving a second audio signal, whereby the second audio signal corresponds to a portion of the first audio signal and is received prior to the corresponding portion of the first audio signal. The microphone may be an internal microphone of the mobile phone or an external microphone of a headphone or earphone. The device further comprises an audio processing unit adapted for processing the second audio signal using the first audio signal, and an output unit for providing the processed audio signal. The audio processing unit comprises herein at least first electronic circuitry for determining a propagation time difference between the first and the second audio signal, second electronic circuitry adapted for modifying the second audio signal by adaptive filtering and additional temporal shifting such that the propagation time difference between the first and the modified second audio signal is substantially compensated, and third electronic circuitry adapted for further modifying and/or inverting the modified second audio signal, resulting in the processed second audio signal. The invention further relates to a mobile device adapted for executing the method for generating and providing an audio signal. Finally, the invention relates also to a software product adapted for configuring a computer or processor to execute the method according to the invention.

BRIEF DESCRIPTION OF THE DRAWINGS

Details and further advantageous embodiments may be better understood by those skilled in the art by reference to the accompanying figures.

DETAILED DESCRIPTION OF EMBODIMENTS

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

Figure 1:
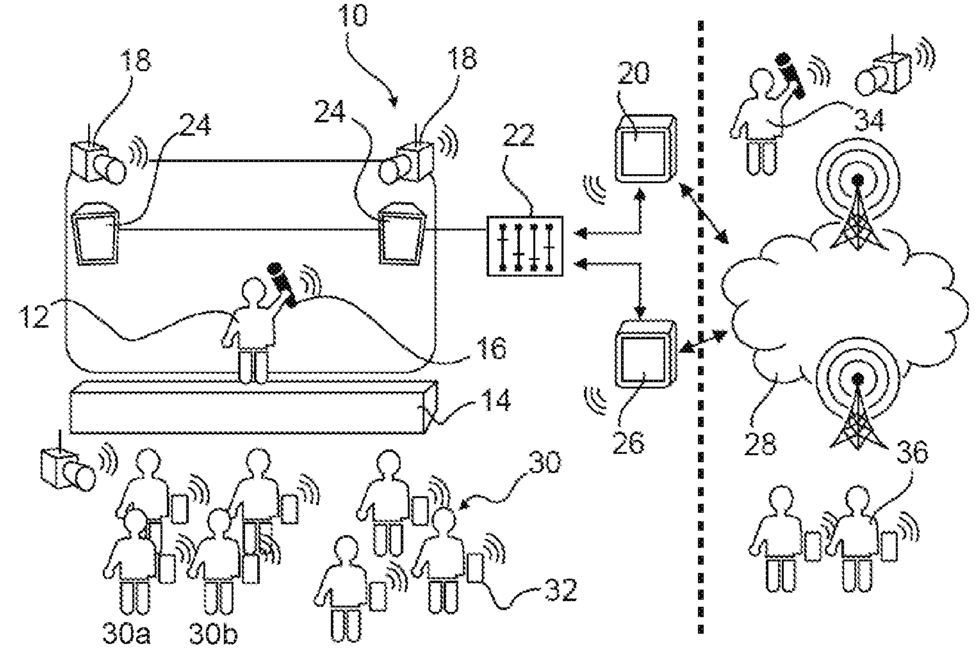
FIG. 1 shows a system overview.

FIG. 1 shows an overview of the system 10, which in this example is used at a live event. At the event, a performing person 12 is on a stage 14. The performing person 12 uses a microphone 16 for recording voice. Further, the person 12 may be recorded by video cameras 18. The microphone 16 and the video cameras 18 transmit their signals wirelessly to a stage receiver 20 which provides the signals to an audio mixer 22. The audio mixer 22 may generate mixed audio signals therefrom.

The audio mixer 22 then transmits the mixed audio signals obtained from the audio signals that were received from the stage receiver 20 to stage loudspeakers 24. The audience 30 hears the sound signal reproduced by these loudspeakers 24. Further, the audio mixer 22 transmits the audio signals to a wireless interface 26, which radiates the signals wirelessly. These signals correspond to an audio signal that may have a plurality of audio tracks.

In addition, the mixed audio signals are in this example transmitted directly or via the wireless interface 26 to a mobile radio network 28 or a similar service network, which also broadcasts the audio signals having one or more audio tracks by a further wireless interface. Furthermore, viewers 30 are depicted who each carry a mobile device 32 according to the invention, which is set up to receive audio signals either directly via the wireless interface 26 or via the mobile radio network 28. In this example it is also possible to use the mobile radio network 28 for providing additional input signals from remote performers 34 to the audio mixer 22, as well as providing the audio and video signals of the performers 12,34 to a remote audience 36. Thus, different artists in a joint performance need not be on the same stage 14 but may be interconnected electronically via the service network 28.

In some embodiments, the invention enables e.g. two viewers 30*a*,30*b* who are at a rock concert near loudspeakers 24 to talk and hear each other, despite a high sound pressure level of the loudspeakers.

Figure 2:
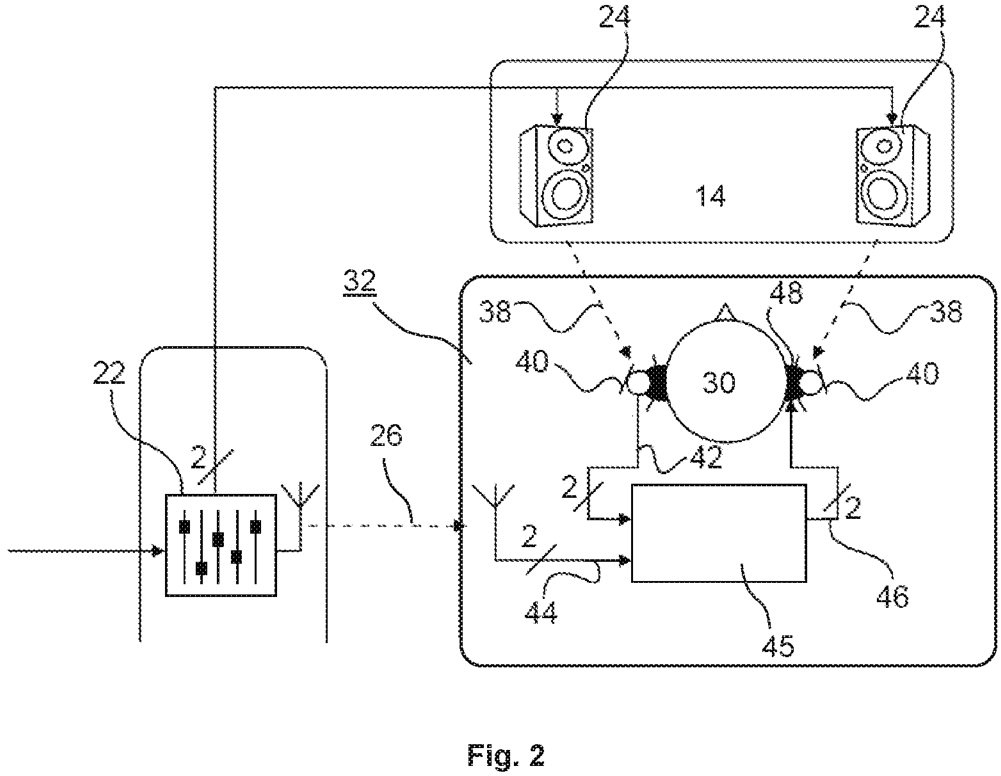
FIG. 2 shows a more detailed schematic structure for executing the method.

FIG. 2 shows a detailed view of a schematic structure for carrying out the method for generating and providing an audio signal. The stage loudspeakers 24 receive audio signals from a mixing console or audio mixer 22 and emit corresponding sound waves 38. These hit microphones 40 that pick them up and convert them into a first audio signal 42. The first audio signal 42 represents ambient sound (AS). In addition, the audio mixer 22 provides audio signals for transmission to the wireless interface 26 or the mobile radio network 28, which may also be considered a wireless interface. These audio signals are received by a reception unit (not depicted) and represent a second audio signal 44. This second audio signal 44 can be used as an Assistive Live Listening Signal (ALLS) The first audio signal 42 and the second audio signal 44 are then processed in an audio processing unit 45 according to the invention. In the audio processing unit 45, first the propagation time difference between the two audio signals is determined and then reduced or eliminated by delaying the second audio signal 44. Additionally, the second audio signal 44 is modified, e.g. by adaptive filtering using the first audio signal 42. Using the first audio signal 42 as a control signal makes the adaptive filter model the acoustic transmission of the first audio signal and output an estimated difference signal between the first audio signal and the second audio signal. In addition, the second audio signal 44 can be further modified. In some embodiments, the modified second audio signal 46 is inverted and is provided as a compensation signal to headphones 48 of viewers 30, since it is suitable for compensating individual ambient sound at live events. In particular, the method according to the invention is better suitable for this than conventional ANC, because with the second signal, a substantial part of the ambient signal is known here before it is picked up by the microphone. Each viewer 30 may wirelessly receive the same second audio signal. Note that while FIG. 2 is simplified for better understanding, the modified second audio signal 46 is preferably provided to the same ear near which the microphone 40 providing the first audio signal 42 is located. In the case of a stereo headphone, two different modified second signals or inverted modified second signals 46 may be provided, one for each ear. In an embodiment, each viewer 30 may individually set one or more parameters and/or select one of several operating modes in order to hear an individual sound.

An advantage of the invention in some embodiments is that also the microphones 40 are located on this headphone 48. Therefore, the distance between the microphones 40 and the user's meatus is substantially known, constant and very small. Thus, the ambient sound 38 picked up by the microphones 40 is substantially identical with the ambient sound that the listener 30 hears despite the headphone, and in particular both have the same phase. Especially in a noisy environment like a rock concert, headphones almost always let a part of the ambient sound through. Phase differences between the ambient sound directly heard and the ambient sound picked up by the microphone and (inversely) reproduced by the headphone have a disturbing effect. Such phase differences are frequency dependent and may already be noticeable e.g. if the distance between the microphone 40 and the ear changes by few centimeters. Therefore, this embodiment has the advantage that the phase of the ambient sound signal picked up by the microphone is known and constant, different from another variant where e.g. a microphone of a smartphone is used. In this way, the sound reproduced by the headphone can be better synchronized with the ambient sound.

Figure 3:
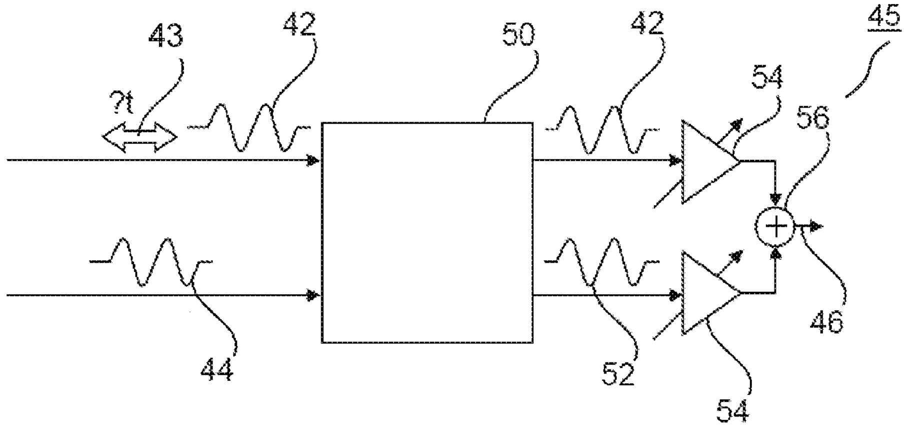
FIG. 3 shows a schematic block diagram of an audio processing unit comprising circuitry for determining and compensating the propagation time difference and circuitry for merging.

FIG. 3 shows a schematic block diagram of the processing unit 45 with a propagation time difference 43 between the first audio signal 42 and the second audio signal 44 and with circuitry 50 for determining and compensating the propagation time difference 43 being depicted. At the output, the propagation time difference 43 between the first audio signal 42 and the second audio signal 44 is at least substantially removed by shifting or modifying the second audio signal 44 to obtain a modified second audio signal 52. In principle, the first audio signal and the modified second audio signal are then amplified by amplifiers 54 that may be adjustable, and finally merged by a merging unit 56 (e.g. adder). Here, the second audio signal 44 may also be inverted (not shown), so that the merging unit 56 acts as a subtractor. Finally, the merged signal 46, or modified second audio signal respectively, that is obtained by the merging (shown here simplified as addition or subtraction) is output. In particular, a difference signal obtained by subtracting the second audio signal from the first audio signal may, in implementations, result from adaptively filtering the second audio signal, e.g. if the first audio signal is used for controlling the adaptive filter.

Figure 4:
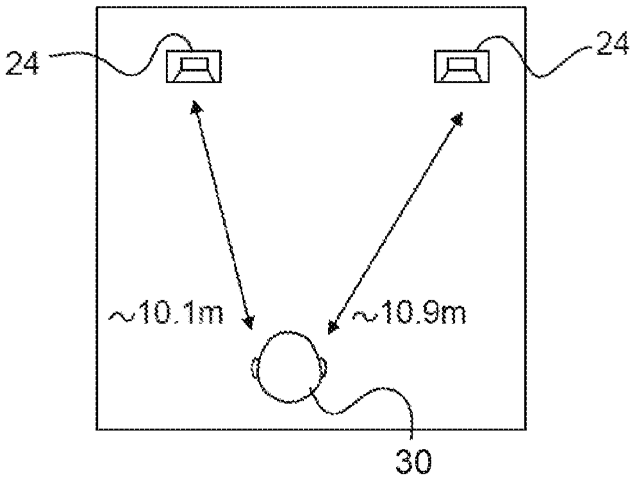
FIG. 4 shows a viewer whose position is asymmetrical to two stage loudspeakers.

FIG. 4 shows the problem that a viewer 30 is positioned asymmetrically with respect to two different stage loudspeakers 24. For example, a distance to the left loudspeaker is 10.1 m while a distance to the right loudspeaker is 10.9 m. The difference of 0.8 m is already a multiple of the wavelength of the sound signal. According to an embodiment, two first audio signals and two second audio signals representing the right channel and the left channel respectively are received. Thus, individual propagation time differences can be determined between a first first audio signal and a first second audio signal for the right channel, as well as between a second first audio signal and a second second audio signal for the left channel. In particular the depicted and very common asymmetric position of the viewer 30 results in different propagation times and different propagation time differences for the left and right sides. In addition, there may be crosstalk as each ear also hears the signal from the other side's speaker. These signals have different propagation times too. By adjusting parameters such as delay appropriately, the second audio signal received via radio can be used to enhance, or compensate respectively, each of the two audio signals of the right channel and the two audio signals of the left channel.

Figure 5:
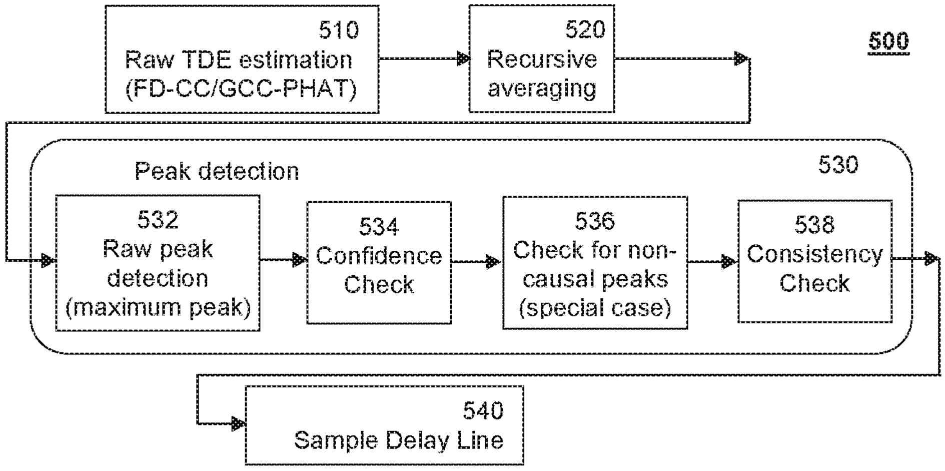
FIG. 5 shows a flowchart of a method for determining the propagation time difference.

FIG. 5 shows exemplarily steps of a method 500 for determining the propagation time difference. There occur uncertainties e.g. due to echoes and reverberation, so that initially a raw time delay estimation (TDE) 510 is performed. Algorithms for this are in principle known, like e.g. Frequency Domain Cross-Correlation (FD-CC) or the Generalized Cross-Correlation with Phase Transform (GCC-PHAT), which is also performed in the frequency domain. The first trends to be more susceptible for errors due to reverberation but yields better results in a noisy environment if pre-filtering is used, while the latter requires more processing power. In the next step, recursive averaging 520 is performed in order to increase the robustness of the method. After that, the temporally averaged cross-correlation is passed to a multi-staged peak detection 530, which comprises first a raw peak detection 532 for detecting a maximum peak and a corresponding propagation time. Then, a confidence check 534 is conducted that compares the maximum peak value with the mean of all positive values of the cross-correlation function. If this ratio is sufficiently large, the result is considered significant and is passed to the next stage. Here, the cross-correlation function is checked 536 for non-causal peaks preceding the dominant peak, which may occur in special cases, so that a first significant peak is not the dominant one. For this, the obtained maximum peak may be compared to the second highest non-causal peak. If this ratio is larger than a threshold value, the maximum peak value is considered valid and is passed to the next stage, where it is compared 538 in a consistency check to the previous maximum peak value. If they are identical sufficiently often, the peak value is accepted as valid and, in this example, applied to a delay line buffer 540. In an embodiment, a counter is incremented each time the values are identical. If the counter reaches a threshold value, the peak value is accepted as valid and applied to the delay line buffer. The delay line buffer delays 540 the samples of the second audio signal 44 in order to temporally align it with the first audio signal 42.

Figure 6:
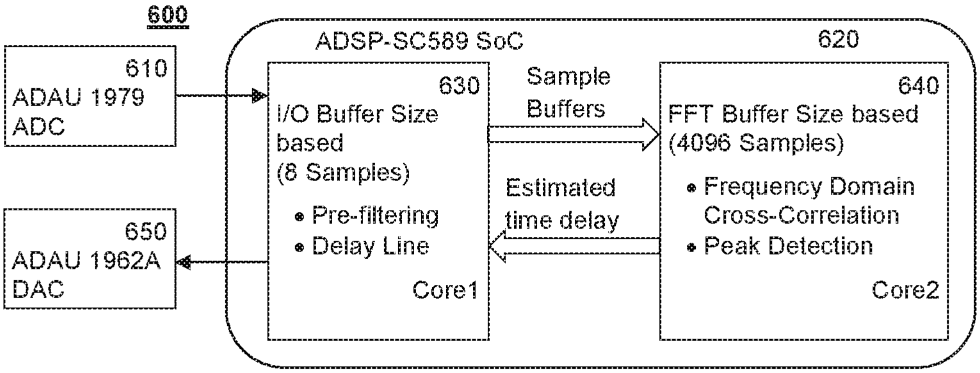
FIG. 6 shows an implementation example for determining and removing a propagation time difference.

FIG. 6 shows a corresponding implementation 600 on an ADSP-SC589 (multicore processor) SoC evaluation board. The reception signal is digitized by an analog-to-digital converter (ADC) 610, e.g. of type ADAU1979. The digitized signal is processed by initial pre-filtering in a first processing core 630 of the processor 620. Each 8 samples (corresponding to the I/O buffer size) are passed to a second processing core 640, which performs a transformation into the frequency domain, the respective cross-correlation in the frequency domain, the multi-stage peak detection 530 and the delay estimation. The second core 640 may operate in units of 4096 samples, corresponding to the FFT buffer size. The resulting estimated delay value is returned to the first core 630, which additionally implements a delay line for the digitized input signals. It is set to a delay according to the estimated delay value. After the set delay, the buffered input signals are read out of the delay buffer again and converted into analog values by a digital-to-analog converter (DAC) 650, e.g. of type ADAU1962A. These analog values are then output.

Figure 7:
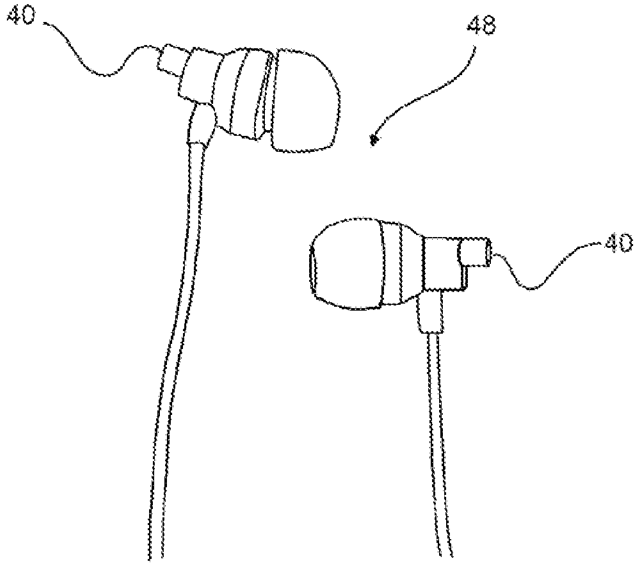
FIG. 7 shows an exemplary headphone having integrated microphones and being adapted for executing the method.

FIG. 7 shows by way of example a schematic view of headphones 48 in the form of earphones according to an embodiment of the invention, which may advantageously be used for the above-described methods and which have on their outside microphones 40 for recording (i.e. detecting) the first audio signal. Alternatively or additionally, also microphones inside the headphone may be used. In a variant, active noise cancelling (ANC) microphones within the headphone that are actually intended for noise cancellation are used in addition to the outside microphones 40. The circuitry or device for generating and providing an audio signal according to the invention may be located within the headphone or in a connected mobile device, e.g. a smartphone.

In an embodiment, such device for generating and providing an audio signal comprises at least one microphone 40 for receiving a first audio signal 42, wherein the microphone 40 is an external microphone of a headphone or earphone, a wireless interface 26 for receiving a second audio signal, an audio processing unit 45 with electronic circuitry for modifying the second audio signal using the first audio signal, e.g. by an adaptive filter for filtering the second audio signal and inverting the filtered second audio signal, and an output unit 85 for outputting the inverted filtered second audio signal towards a sound transducer. The audio processing unit 45 may comprise an electronic circuit 50 for determining and modifying the propagation delay difference, and an adaptive filter which in principle fulfils a function comparable to the amplifiers 54 and the adder/subtractor 56. Optionally, the device may comprise further components, e.g. a pre-filter, ADC, DAC, etc. Single, several or all of the above-mentioned components may be implemented on one or more software-configurable processors. In the headphone shown in FIG. 7, some portions of the device may be present twice, namely once for each side. Other portions are usually needed only once, e.g. a reception unit for the wireless interface.

Figure 8:
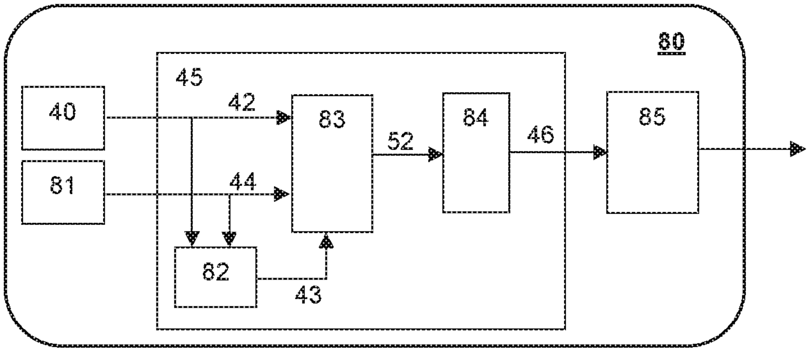
FIG. 8 shows a block diagram of a device for providing an audio signal.

FIG. 8 shows a block diagram of a device 80 for providing an audio signal, in an embodiment. The device comprises a microphone 40 adapted for recording a first audio signal 42 and a wireless interface module, e.g. wireless reception unit 81, for receiving a second audio signal 44 through radio signals. Further, the device 80 comprises an audio processing unit 45 for merging the first audio signal with the second audio signal, and an output unit 85 for providing the merged audio signal 46 to an output. The audio processing unit 45 in this example is a device comprising first electronic circuitry 82 for determining a propagation time difference 43 between the first and second audio signals 42,44, second electronic circuitry 83 for modifying the second audio signal 44 by adaptive filtering and temporal shifting or phase shifting based on the determined propagation time difference 43, and third electronic circuitry 84 for further modifying the modified second audio signal. The further modifying may comprise inverting. Optionally, the third electronic circuitry 84 may comprise further components or fulfil further functions, respectively, e.g. adding the second audio signal. The second electronic circuitry 83 may comprise e.g. a delay line and an adaptive filter or the amplifiers 54 and the adder or subtractor 56. The merged audio signal 46 is output via an output interface 85, e.g. towards a sound transducer within the headphone 48.

Figure 9:
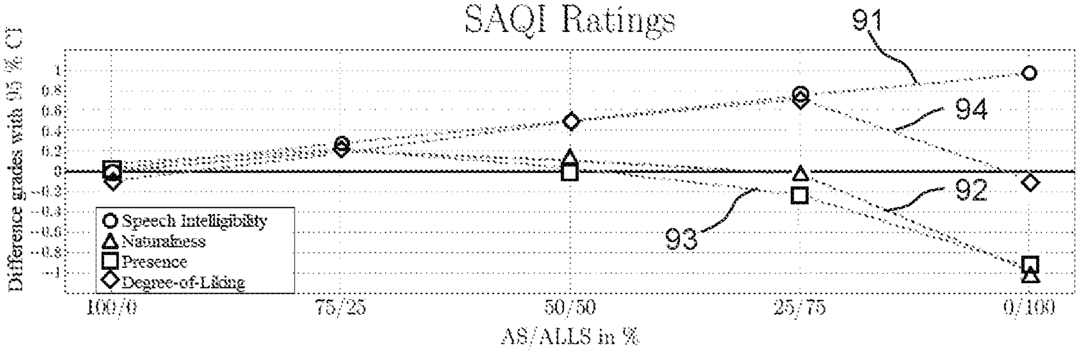
FIG. 9 shows various mixing ratios between the first and second audio signal in a merged audio signal.

In an embodiment, the first and second audio signals may be additively combined to obtain the modified second audio signal 46. Both parts may be differently weighted herein, leading to different mixing ratios. FIG. 9 shows various mixing ratios between the first and second audio signal in the merged audio signal, and the empirically determined assessment parameters speech intelligibility 91, naturalness 92, presence 93 and an overall degree-of-liking 94. The mixing ratio between the first and second audio signal may be adjustable manually or automatically, depending on an ambient sound level. A preferred mixing ratio (AS/ALLS) is in a range of 40/60 to 20/80, particularly preferred 25/75 since this provides a particularly pleasant listening experience for a viewer. Therefore, in one embodiment, such preferred mixing ratio is set, e.g. by setting the adjustable amplifiers 54 shown in FIG. 3 such that for a mixing ratio of 25/75 the proportion of ALLS in the output signal is 75%. In general, speech intelligibility 91 increases continuously with the percentage of ALLS, i.e. the second audio signal 44. This can be expected, since here no influences of the room like e.g. echoes are contained, so that these influences are increasingly eliminated from the merged signal. On the other hand, naturalness 92 and presence 93 are perceived in a range around 75/25 as optimal, and in a range above 25/75 are below the value of pure ambient sound signal AS. However, the overall degree-of-liking 94 increases until a range with a mixing ratio of 25/75.

Figure 10:
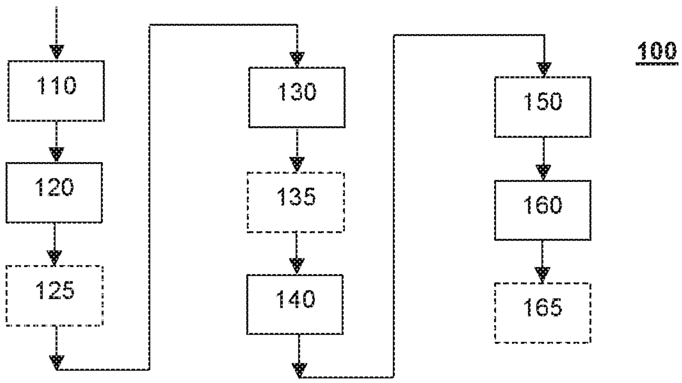
FIG. 10 shows a flowchart of a method for generating and providing an audio signal.

FIG. 10 shows a flowchart of a method 100 for generating and providing an audio signal, in an embodiment. The method 100 comprises receiving 110 a first audio signal via a microphone, wherein the microphone is an external microphone of a headphone or earphone. The first audio signal comprises a signal portion that is reproduced via loudspeakers. The method further comprises receiving 120 a second audio signal via a wireless interface. The second audio signal corresponds to the portion of the first audio signal that is reproduced via loudspeakers, but it is received prior to the corresponding portion of the first audio signal. Then, a propagation time difference between the first audio signal and the second audio signal is determined 130. The method further comprises modifying 140 the second audio signal by adaptive filtering and temporal shifting such that the propagation time difference between the first and second audio signal is substantially compensated, wherein the adaptive filtering models an acoustic transmission of the first audio signal and wherein a modified second audio signal is obtained. The modified second audio signal is inverted 150, and the inverted modified second audio signal is provided 160 via the headphone or earphone. In an optional step 165, also the second audio signal is provided via the headphone or earphone. In another optional step 125, a data signal comprising information about the two or more audio tracks of the second audio signal is additionally received via the wireless interface. In another optional step 135, at least one of the first and the second audio signal is further modified prior to the adaptive filtering. In a different embodiment, the step 150 of inverting the modified second audio signal is omitted, and the non-inverted modified second audio signal is provided 160 via the headphone or earphone.

Figure 11:
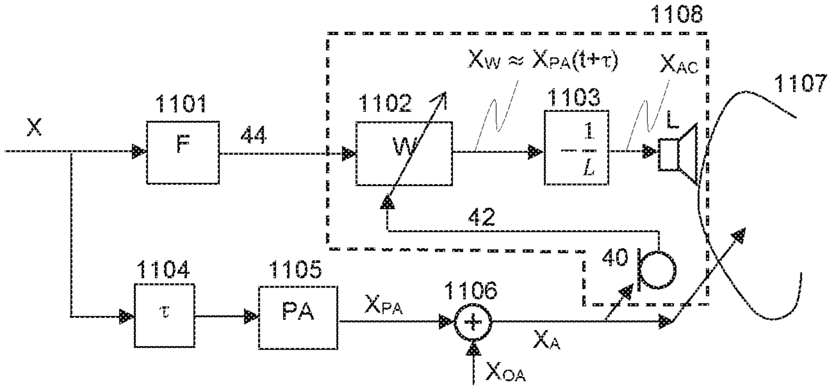
FIG. 11 shows a block diagram of sound transmission.

FIG. 11 shows a block diagram of sound transmission, according to an embodiment. A primary audio signal X is transmitted twice, namely as a sound signal via loudspeakers 1105 of a Public Address (PA) system and as a radio signal via radio transmission 1101. The air-borne transmission of the sound signal requires a time $\tau$ that is modeled herein as a delay 1104. The sound signal of the loudspeakers $X_{PA}$ is often superimposed 1106 by other ambient sounds $X_{OA}$ with arbitrary delay, which results in the final ambient sound signal $X_A$ that arrives at the user's ear 1107. Near the user's ear, this signal is picked up by the external microphone 40 of a headphone or earphone to generate the first audio signal 42. The first audio signal 42 apparently comprises a portion that is reproduced via the loudspeakers 1105. The first audio signal 42 is provided to an adaptive filter 1102, where it is preferably used for adapting the filter, i.e. as a target or desired signal of the adaptive filter. The input signal that is actually filtered by the adaptive filter 1102 is the second audio signal 44 received via radio transmission 1101. In this configuration, the adaptive filter 1102 provides an output signal $X_W$ that approximates the sound signal of the loudspeakers $X_{PA}$ since it is common to both its input signals. However, since the filtering is applied to the second audio signal 44 that is available before the first audio signal 42, the output signal $X_W$ approximates the loudspeaker sound signal $X_{PA}$ (t+$\tau$), i.e. a future loudspeaker sound signal that has not yet been picked up by the microphone 40. It is used as input signal for an Active Noise Cancellation (ANC) block 1103, which generates an inverse signal $X_{AC}$ that is played back via loudspeaker L of the headphone or earphone. The inverse signal $X_{AC}$ therefore cancels a portion of the ambient sound signal $X_A$ that also arrives at the user's ear 1107, namely the portion that originates from the PA loudspeaker 1105. However, different from conventional ANC that operates in real-time and is therefore capable of cancelling low frequencies only, ANC block 1103 receives its input signal earlier (i.e. before microphone 40 picks up the corresponding sound wave), and thus can use this time advantage for generating counter waves even for higher frequencies, far beyond 1 kHz. Depending on the delay $\tau$ 1104, frequencies up to e.g. 5 kHz, 10 kHz or 20 kHz may be cancelled. Thus, at least that portion of the ambient sound signal $X_A$ that originates from the loudspeaker signal $X_{PA}$ can be completely or almost completely cancelled at the user's ear. The cancellation signal $X_{AC}$ reproduced by the headphone or earphone loudspeaker L can be superimposed by other signals, e.g. a telephone signal, so that the user may conduct a telephone call while being at the live event.

Generally, embodiments using an external microphone of an earphone or headphone are particularly advantageous if the first and second audio signal are added, while in other cases such as radio-assisted ANC in principle also a microphone of a different mobile device can be used.

In a variant, the invention relates to a method for emitting an audio signal with steps of receiving from an audio mixer a first audio signal having two or more audio tracks, generating or determining information about the two or more audio tracks of the first audio signal, and emitting the received first audio signal as a second audio signal together with a data signal via a wireless interface, the second audio signal having two or more audio tracks and the data signal comprising the generated or determined information. In an embodiment, the wireless interface is a WLAN interface or mobile radio network interface according to the 3G, 4G or 5G standard. In another embodiment, the invention relates to a software product comprising instructions that when executed on a computer or processor configure the computer or processor to execute a method as described above. In a further embodiment, the invention relates to a device for emitting an audio signal that is adapted for executing the method, in particular a mixing console or mixer.

In an embodiment, the invention relates to a storage device or storage medium having stored thereon software instruction for configuring a computer or processor to execute a method as described above. In an embodiment, the invention relates to a system with at least one device for providing an audio signal, as described above, and a device for emitting an audio signal, as described above.

Embodiments described above may be combined if such combination is meaningful. Devices and units described above may be implemented in hardware, software or a combination thereof, such as one or more software-configured processors.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

The invention claimed is:

1. A method for generating and providing an audio signal, comprising:

receiving a first audio signal via a microphone, wherein the microphone is an external microphone of a headphone or earphone, and wherein the first audio signal comprises a portion that is reproduced via loudspeakers;

receiving a second audio signal via a wireless interface, the second audio signal corresponding to the portion that is reproduced via loudspeakers and being received prior to the corresponding portion of the first audio signal;

determining a propagation time difference between the first audio signal and the second audio signal;

modifying the second audio signal by adaptive filtering and temporal shifting such that the propagation time difference between the first and second audio signal is substantially compensated, wherein the adaptive filtering models an acoustic transmission of the first audio signal and wherein a modified second audio signal is obtained;

inverting the modified second audio signal, wherein an inverted modified second audio signal is obtained; and providing the inverted modified second audio signal via the headphone or earphone.

2. The method according to claim 1;

wherein the second audio signal is additionally provided via the headphone or earphone.

3. The method according to claim 1;

wherein the wireless interface is a WLAN interface or a mobile network interface according to the 3G, 4G, or 5G standard.

4. The method according to claim 1;

wherein said determining the propagation time difference comprises a cross-correlation in a frequency domain.

5. The method according to claim 1;

wherein the second audio signal has two or more audio tracks, and said modifying by adaptive filtering comprises attenuating, removing, or partially removing at least one audio track of the second audio signal.

6. The method according to claim 5;

wherein a data signal is additionally received via the wireless interface, the data signal comprising information about the two or more audio tracks of the second audio signal.

7. The method according to claim 1, further comprising:

a step of further modifying at least one audio signal of the first and second audio signals prior to the adaptive filtering;

wherein the further modifying comprises adding, partially adding, amplifying, attenuating, removing, partially removing, or a combination thereof, at least one adjustable frequency or at least one adjustable frequency range to or from the at least one audio signal.

8. A mobile device configured to execute the method according to claim 1.

9. A non-transient computer-readable storage medium having stored thereon instructions configured to instruct a computer or computer processor to execute the method according to claim 1.

10. A computer software product adapted for configuring a computer or computer processor to execute the method of claim 1.

11. The software product according to claim 10;

wherein the computer or computer processor is part of a mobile electronic device.

12. A device for generating and providing an audio signal, the device comprising:

a microphone configured to record a first audio signal, wherein the microphone is an external microphone of a headphone or earphone;

a wireless interface module configured to receive a second audio signal, wherein the second audio signal corresponds to a portion of the first audio signal and is received prior to the corresponding portion of the first audio signal;

an audio processing unit configured to process the second audio signal using the first audio signal; and an output unit configured to provide the processed second audio signal to the headphone or earphone for being reproduced;

wherein the audio processing unit comprises:

first electronic circuitry configured to determine a propagation time difference between the first and second audio signal;

second electronic circuitry configured to modify the second audio signal by adaptive filtering and temporal shifting, such that the determined propagation time difference between the first and the second audio signal is compensated, wherein a modified second audio signal is obtained; and third electronic circuitry configured to invert the modified second audio signal, wherein the processed second audio signal is obtained.

13. The device according to claim 12;

wherein the second audio signal is additionally reproduced via the headphone or earphone.

14. The device according to claim 12;

wherein the propagation time difference is determined by a cross-correlation in the frequency domain.

15. A method for generating and providing an audio signal, comprising:

receiving a first audio signal via a microphone, wherein the first audio signal comprises a portion that is reproduced via loudspeakers;

receiving a second audio signal via a wireless interface, the second audio signal corresponding to the portion that is reproduced via loudspeakers and being received prior to the corresponding portion of the first audio signal;

determining a propagation time difference between the first audio signal and the second audio signal;

modifying the second audio signal, the modifying comprising adaptive filtering and temporal shifting such that the propagation time difference between the first and second modified audio signal is substantially compensated, wherein the adaptive filtering models an acoustic transmission of the first audio signal, and wherein a modified second audio signal is obtained; and providing the modified second audio signal via a headphone or earphone.

16. The method according to claim 15;

wherein the wireless interface is a WLAN interface or a mobile network interface according to the 3G, 4G, or 5G standard.

17. The method according to claim 15;

wherein said determining the propagation time difference comprises a cross-correlation in a frequency domain.

18. The method according to claim 15;

wherein the second audio signal has two or more audio tracks, and said modifying by adaptive filtering comprises attenuating, removing, or partially removing at least one audio track of the second audio signal.

19. The method according to claim 18;

wherein a data signal is additionally received via the wireless interface, the data signal comprising information about the two or more audio tracks of the second audio signal.

20. The method according to claim 15, further comprising:

a step of further modifying at least one audio signal of the first and the second audio signals prior to the adaptive filtering;

wherein the further modifying comprises adding, partially adding, amplifying, attenuating, removing, partially removing, or a combination thereof, at least one adjustable frequency or at least one adjustable frequency range to or from the at least one audio signal.

21. The method according to claim 15, further comprising steps of:

receiving a user input for selecting an operating mode; and depending on the received user input, inverting the modified second audio signal;

wherein if the user input corresponds to a first operating mode, the modified second audio signal is not inverted before being provided via the headphone or earphone, and if the user input corresponds to a second operating mode, the modified second audio signal is inverted before being provided via the headphone or earphone.

22. A device for generating and providing an audio signal, the device comprising:

a microphone configured to record a first audio signal;

a wireless interface module configured to receive a second audio signal, wherein the second audio signal corresponds to a portion of the first audio signal and is received prior to the corresponding portion of the first audio signal;

an audio processing unit configured to process the second audio signal using the first audio signal; and an output unit configured to provide the processed second audio signal to a headphone or earphone for being reproduced;

wherein the audio processing unit comprises:

first electronic circuitry configured to determine a propagation time difference between the first and second audio signal;

second electronic circuitry configured to modify the second audio signal by adaptive filtering and temporal shifting, such that the determined propagation time difference between the first and the second audio signal is compensated, wherein the processed second audio signal is obtained.

23. The device according to claim 22;

wherein the second audio signal is additionally reproduced via the headphone or earphone.

24. The device according to claim 22;

wherein the propagation time difference is determined by a cross-correlation in the frequency domain.

25. The method according to claim 22, further comprising:

user input means configured to receive user input;

operating mode control means configured to select an operating mode, based on the user input received by the user input means; and third electronic circuitry configured to invert the modified second audio signal, depending on the selected operating mode;

wherein in a first operating mode the modified second audio signal is not inverted and the processed second audio signal corresponds to the modified second audio signal, and wherein in a second operating mode the modified second audio signal is inverted and the processed second audio signal corresponds to an inverted modified second audio signal.

* * * * *